US012584911B2

(12) United States Patent
Hefner

(10) Patent No.: US 12,584,911 B2
(45) Date of Patent: Mar. 24, 2026

(54) MULTIPLEX DETECTION IN HIGH RESOLUTION DEVICES THROUGH MEASUREMENT OF LOCALIZED FLUORESCENCE RATIOS

(71) Applicant: Bio-Rad Laboratories, Inc., Hercules, CA (US)

(72) Inventor: Eli Hefner, Fairfield, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 620 days.

(21) Appl. No.: 18/083,131

(22) Filed: Dec. 16, 2022

(65) Prior Publication Data

US 2023/0194517 A1     Jun. 22, 2023

Related U.S. Application Data

(60) Provisional application No. 63/292,363, filed on Dec. 21, 2021.

(51) Int. Cl.
*G01N 33/543* (2006.01)
*B01L 3/00* (2006.01)
*G01N 21/64* (2006.01)

(52) U.S. Cl.
CPC .. *G01N 33/54386* (2013.01); *B01L 3/502761* (2013.01); *G01N 21/6428* (2013.01);
(Continued)

(58) Field of Classification Search
CPC ... G01N 2021/6439; G01N 2021/6441; G01N 21/6428; G01N 21/6458; G01N 21/648;
(Continued)

(56) References Cited

U.S. PATENT DOCUMENTS 10,093,967 B2    10/2018  Walter et al.
2009/0004757 A1    1/2009  Yguerabide et al.
(Continued)

FOREIGN PATENT DOCUMENTS

WO    2010/085548 A3    7/2010
WO    2013/153911 A1    10/2013
(Continued)

OTHER PUBLICATIONS

Black, S., Phillips, D., Hickey, J.W et al. CODEX multiplexed tissue imaging with DNA-conjugated antibodies. Nat Protoc 16, 3802-3835 (2021). https://doi.org/10.1038/s41596-021-00556-8 (Year: 2021).*
(Continued)

*Primary Examiner* — Dean Kwak
(74) *Attorney, Agent, or Firm* — Kilpatrick Townsend & Stockton LLP

(57) ABSTRACT

Systems and methods for multiplex detection through measurement of localized fluorescence ratios are disclosed herein. This can include creating a plurality of capture structures that each include a detection portion that can couple with a target analyte and a stem that can include a capture structure code uniquely identifying a type of the capture structure. The capture structures can be attached to a sample surface and mixed with a sample containing a plurality of target analytes. A location and the capture structure code of each of the capture structures can be determined. A location at which a target analyte is bound to one of the capture structures can be identified, and the target analyte can be determined based on the capture structure code of the capture structure at the location at which the target analyte is bound to one of the capture structures.

19 Claims, 7 Drawing Sheets

(52) U.S. Cl.
CPC .. *G01N 21/6458* (2013.01); *B01L 2200/0652* (2013.01); *B01L 2300/0654* (2013.01); *B01L 2300/0681* (2013.01); *G01N 2021/6439* (2013.01)

(58) Field of Classification Search
CPC ......... G01N 2458/10; G01N 33/54373; G01N 33/54386; B01L 2200/0652; B01L 2300/0654; B01L 2300/0681; B01L 3/502761; C12Q 1/6804; C12Q 1/682; C12Q 2563/107; C12Q 2565/102
See application file for complete search history.

(56) References Cited

U.S. PATENT DOCUMENTS

| | | |
|---|---|---|
| 2012/0256102 A1 | 10/2012 | Younghoon et al. |
| 2016/0161472 A1 | 6/2016 | Jungmann et al. |
| 2018/0238808 A1 | 8/2018 | Kilfeather et al. |
| 2018/0258469 A1 | 9/2018 | Johnson-Buck et al. |
| 2019/0003973 A1 | 1/2019 | Lin et al. |
| 2019/0032120 A1 | 1/2019 | Walter et al. |
| 2019/0048415 A1 | 2/2019 | Walter et al. |
| 2019/0187031 A1 | 6/2019 | Johnson-Buck et al. |

| | | |
|---|---|---|
| 2019/0339266 A1 | 11/2019 | Liu |
| 2020/0209229 A1 | 7/2020 | Strong et al. |
| 2021/0116369 A1 | 4/2021 | Thrush et al. |
| 2021/0189475 A1* | 6/2021 | Tentori ................. C12Q 1/6841 |
| 2021/0239707 A1 | 8/2021 | Loboda et al. |

FOREIGN PATENT DOCUMENTS

| | | |
|---|---|---|
| WO | 2017/041030 A1 | 3/2017 |
| WO | 2020/023503 A1 | 1/2020 |
| WO | 2022/182635 A1 | 9/2022 |

OTHER PUBLICATIONS

Johnson-Buck, A et al.; "Kinetic fingerprinting to identify and count single nucleic acids"; *Nature Biotechnology*; vol. 33, No. 7, Jul. 2015; pp. 730-732.

International Search Report and Written Opinion in International Application PCT/US2022/053206 mailed Mar. 15, 2023; 10 pages.

Black, S. et al.; "CODEX multiplexed tissue imaging with DNA-conjugated antibodies"; *Nature Protocols*; vol. 16, No. 8; Jul. 2, 2021; pp. 3802-3835.

Extended European Search Report in EP Appln. 22912327.8 mailed Nov. 18, 2025; 9 pages.

\* cited by examiner

―500

| Location | Channel 1 | Channel 2 | Channel 3 |
|----------|-----------|-----------|-----------|
| 1 | 3 | 1 | 3 |
| 2 | 1 | 2 | 1 |
| 3 | 1 | 1 | 2 |
| 4 | 3 | 3 | 3 |
| 5 | 3 | 3 | 2 |
| 6 | 2 | 1 | 1 |

700

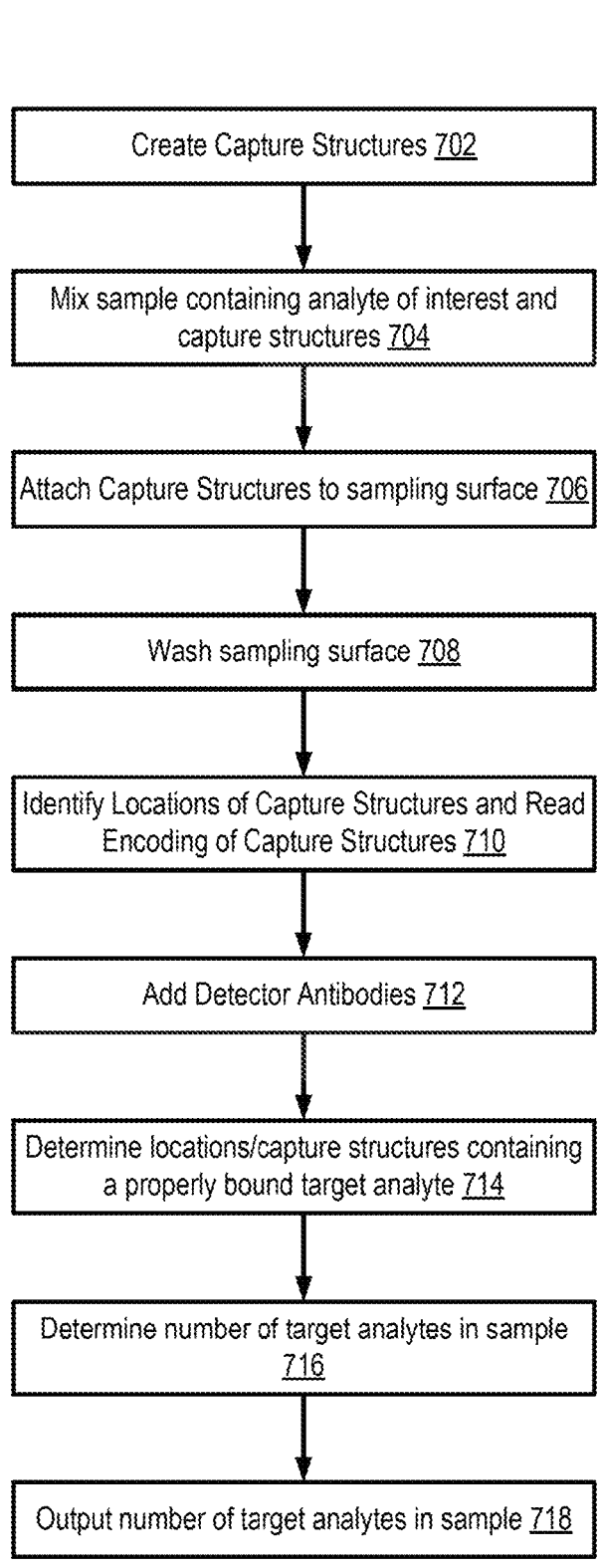

Create Capture Structures 702

↓

Mix sample containing analyte of interest and capture structures 704

↓

Attach Capture Structures to sampling surface 706

↓

Wash sampling surface 708

↓

Identify Locations of Capture Structures and Read Encoding of Capture Structures 710

↓

Add Detector Antibodies 712

↓

Determine locations/capture structures containing a properly bound target analyte 714

↓

Determine number of target analytes in sample 716

↓

Output number of target analytes in sample 718

Figure 7

MULTIPLEX DETECTION IN HIGH RESOLUTION DEVICES THROUGH MEASUREMENT OF LOCALIZED FLUORESCENCE RATIOS

CROSS-REFERENCE TO RELATED PATENT APPLICATIONS

The present patent application claims benefit of priority to U.S. Provisional Patent Application No. 63/292,363, filed Dec. 21, 2021, the entirety of which is hereby incorporated by reference for all purposes.

BACKGROUND OF THE INVENTION

Detection and/or characterization of analytes in a solution has many applications in both research and medical fields. This can include the detection and quantifying of analytes in a complex mixture. The successful detection of certain analytes can enable the detection, and in some instances the early detection of different diseases or disease states. Such early detection of different diseases and/or disease states can be outcome determinative in the effective treatment of those diseases and/or disease states.

Although the detection of analytes can provide a powerful tool, the utility of this tool is currently subject to limitations that prevent its more widespread and beneficial use. Accordingly, further development and improvements for detecting analytes are desired.

BRIEF SUMMARY OF THE INVENTION

One aspect of the present disclosure relates to a method for detecting analyte. The method includes creating a plurality of capture structures, each of the plurality of capture structures including a detection portion and a stem. In some embodiments, the detection portion can couple with a target analyte, and/or in some embodiments the stem can include a capture structure code uniquely identifying a type of the capture structure. The method can include attaching each of the capture structures to a sample surface, mixing the plurality of capture structures with a sample containing a plurality of target analytes, determining a location of each of the capture structures on the sample surface, reading the capture structure code of each of the capture structures, determining a location at which a target analyte is bound to one of the capture structures, and determining the target analyte based on the capture structure code of the capture structure at the location at which the target analyte is bound to one of the capture structures. In some embodiments, at least some of the plurality of target analytes bind to detection portions of the plurality of capture structures.

In some embodiments, each of the target analytes includes at least one of: a protein; or a strand of nucleic acid. In some embodiments, the detection portion of at least some of the capture structures includes an antibody. In some embodiments, the capture structure code of each type of capture structure includes a plurality of flowers. In some embodiments, each of the plurality of flowers includes a piece of nucleic acid coupled to at least one detectable molecule.

In some embodiments, the at least one detectable molecule can be a fluorophore.

In some embodiments, each of the plurality of flowers includes a piece of polymer coupled to at least one detectable molecule. In some embodiments, each of the plurality of flowers includes one of: a single flower; or a cluster of flowers. In some embodiments, the flowers are coupled to the stem via at least one branch.

In some embodiments, the at least one branch includes a strand of nucleic acid. In some embodiments, the strand of nucleic acid can have a known length and can attach a desired number of flowers. In some embodiments, the strand of nucleic acid includes at least one of: a strand of DNA; or a strand of RNA. In some embodiments, the at least one branch includes a polymer of known length and can attach a desired number of flowers.

In some embodiments, the plurality of flowers include at least two colors of flowers. In some embodiments, the flowers of each of the at least two colors are coupled to the stem via a unique at least one branch. In some embodiments, reading the capture structure code of each of the capture structures includes: for the location of each of the capture structures on the sample surface, gathering light from the flowers coupled to the stem of the capture structure at that location, and determining a number and color of flowers attached to the stem of the capture structure. In some embodiments, the light from the flowers coupled to the stem of the capture structure at that location is gathered by a detector.

In some embodiments, determining the number and color of flowers attached to the stem of the capture structure includes evaluating a plurality of channels of data from the detector. In some embodiments, evaluating the plurality of channels of data from the detector includes evaluating light intensity at locations of capture structures attached to the sample surface in each of the plurality of channels.

In some embodiments, the method includes determining a number of target analytes in the sample. In some embodiments, determining the number of target analytes in the sample includes: determining the number of capture structures containing target analytes, determining the capture structure code of those capture structures, grouping capture structures having a common capture structure code, and counting the number of capture structures in each group. In some embodiments, the method further includes outputting the number of target analytes in the sample.

In some embodiments, each type of capture structure is associated with a unique combination of number of types of flowers. In some embodiments, a first type of capture structure includes a first number of a first type of flowers and a second number of a second type of flowers. In some embodiments, a second type of capture structure includes a third number of the first type of flowers, and a fourth number of a third type of flowers. In some embodiments, the second type of capture structure includes none of the second type of flowers.

One aspect of the present relates to a system for detecting analyte. The system includes a sample plate that can hold a sample on a sample surface. The sample plate can include a plurality of capture structures attached to the sample surface. In some embodiments, each of the plurality of capture structures can include a detection portion that can couple with a target analyte, and a stem including a capture structure code uniquely identifying a type of the capture structure. The system can include a plurality of target analytes. In some embodiments, at least some of the plurality of target analytes bind to the detection portions of the plurality of capture structures. The system can include an excitation source that can generate excitation energy, a detector that can detect light emitted by the sample, and a processor. The process can determine a location of each of the capture structures on the sample surface, read the capture structure code of each of the capture structures, determine a location at which a target analyte is bound to one of the capture structures, and determine the target analyte based on the capture structure code of the capture structure at the location at which the target analyte is bound to one of the capture structures.

In some embodiments, each of the target analytes includes at least one of: a protein; or a strand of nucleic acid. In some embodiments, the detection portion of at least some of the capture structures includes an antibody. In some embodiments, the capture structure code of each type of capture structure includes a plurality of flowers. In some embodiments, each of the plurality of flowers includes a piece of nucleic acid coupled to at least one detectable molecule. In some embodiments, the at least one detectable molecule can be a fluorophore. In some embodiments, each of the plurality of flowers includes a piece of polymer coupled to at least one detectable molecule. In some embodiments, each of the plurality of flowers includes one of: a single flower; or a cluster of flowers.

In some embodiments, the flowers are coupled to the stem via at least one branch. In some embodiments, the at least one branch includes a strand of nucleic acid. In some embodiments, the strand of nucleic acid has a known length and can attach a desired number of flowers. In some embodiments, the strand of nucleic acid includes at least one of: a strand of DNA; or a strand of RNA. In some embodiments, the at least one branch includes a polymer of known length and can attach a desired number of flowers.

In some embodiments, the plurality of flowers includes at least two colors of flowers. In some embodiments, the flowers of each of the at least two colors are coupled to the stem via a unique at least one branch. In some embodiments, reading the capture structure code of each of the capture structures includes for the location of each of the capture structures on the sample surface, gathering light from the flowers coupled to the stem of the capture structure at that location, and determining a number and color of flowers attached to the stem of the capture structure. In some embodiments, the light from the flowers coupled to the stem of the capture structure at that location is gathered by a detector.

In some embodiments, determining the number and color of flowers attached to the stem of the capture structure includes evaluating a plurality of channels of data from the detector. In some embodiments, evaluating the plurality of channels of data from the detector includes evaluating light intensity at locations of capture structures attached to the sample surface in each of the plurality of channels.

In some embodiments, the processor can further determine a number of target analytes in the sample. In some embodiments, determining the number of target analytes in the sample includes determining the number of capture structures containing target analytes, determining the capture structure code of those capture structures, grouping capture structures having a common capture structure code, and counting the number of capture structures in each group.

In some embodiments, the processor can further output the number of target analytes in the sample. In some embodiments, each type of capture structure is associated with a unique combination of number of types of flowers. In some embodiments, a first type capture structure includes a first number of a first type of flowers and a second number of a second type of flowers. In some embodiments, a second type of capture structure includes a third number of the first type of flowers, and a fourth number of a third type of flowers. In some embodiments, the second type of capture structure includes none of the second type of flowers.

BRIEF DESCRIPTION OF THE DRAWINGS

FIG. 7 is a flowchart illustrating one embodiment of a process for multiplex detection.

DETAILED DESCRIPTION OF THE INVENTION

Figure 1:
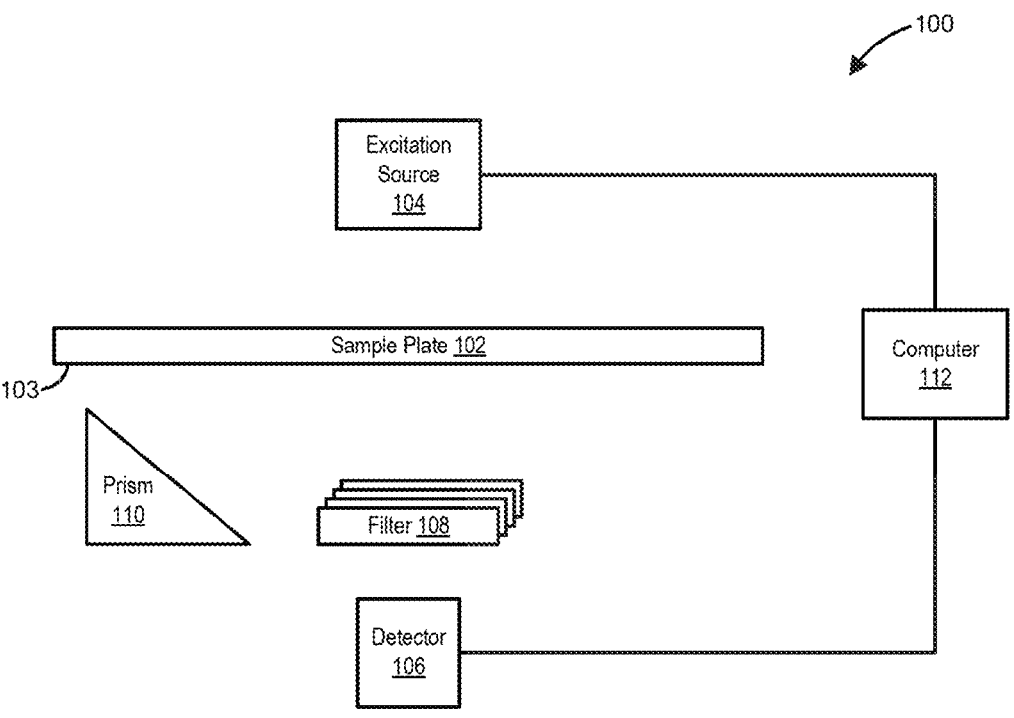
FIG. 1 is a schematic illustration of one embodiment of an imaging system for multiplex detection.

Current technology for the detection of certain analytes (e.g. proteins) may be hindered by a variety of limitations. One of the major limitations of current technology for protein detection is the inability to easily identify multiple analytes within the same field. At present, the ability to simultaneously identify multiple analytes is limited. Attempts have been made at performing the simultaneous detection via, for example, the use of multiple unique dyes, or by spatially restricting a capture component. However, each of these solutions has provided unsatisfactory results.

For example, the utilization of different dyes to detect different analytes is limited by the need to have corresponding excitation and measurement sources for each dye, and by the spectral overlap between dyes. The need for unique excitation and measurement sources increases both the size and the cost of a detection device. Further, spectral overlap between dies limits the number of analytes that can be simultaneously detected and can create inaccurate results.

Spatially restricting the capture component is likewise unsatisfactory as this increases the complexity of the assay. Specifically, this requires the pre-spotting of capture components, such as those used in Single Molecule Recognition through Equilibrium Poisson Sampling (SIMREPS), into a well-defined array. This increased complexity also leads to numerous manufacturing issues. Accordingly, current solutions for simultaneous detection of multiple analytes are unsatisfactory.

The present invention relates to a multiplex analyte assay that enables detection of multiple analytes without the complexities and difficulties of previous solutions. These analytes can include any molecule for which a binding partner exists or is developed. These analytes can include, for example, one or several: nucleic acids, toxins, hormones, metabolites, and/or proteins. In some embodiments, for example, a sample can include analytes including both one or several nucleic acids and one or several proteins. Although the minimum level of an analyte for detection can vary, for example, based on the quality of the binding partner to that analyte, this detection level can, in some instances, be less than, for example, 1,000 nanograms/mL, 500 nanograms/mL, 100 nanograms/mL, 10 nanograms/mL, 1 nanogram/mL, 1 picogram/mL, or the like.

The present multiplex analyte assay can enable detection of multiple analytes in randomly or semi-randomly distributed detection capture components, such as, for example, SIMREPS capture components.

Aspects disclosed herein relate to creation and/or use of a capture structure code, also referred to herein as a barcode, that can be a spatially restricted capture structure code. The capture structure code can identify an associated detection structure and/or capture structure of the system, such as a SIMREPS detection and/or capture structure. For example, each of a plurality of types of detection and/or capture components can have a unique, capture structure code.

In some embodiments, each capture structure can include a stem that can connect to a sample surface and to a detection portion. The stem can be a piece of nucleic acid and/or non-nucleic acid polymer, a polypeptide, one or several plastics such as polypropylene, polycarbonate, polystyrene, or the like, and/or a multicomponent carbon chain. In some embodiments, the stem can be anything that can affix one or several branches, can bind to the sample surface, and can bind to the detection portion. In some embodiments, the stem further keeps the detection portion, any subsequently bound target analyte and detector antibodies sufficiently close to the sample surface to enable imaging via Total Internal Reflection Fluorescence (TIRF) Microscopy.

The stem can connect to the sample surface in one of several ways. In some embodiments, for example, the stem can connect to the sample surface via, for example, a protein such as biotin and/or streptavidin, via NHS ester, click chemistry, maleimide chemistry, or the like. The stem can connect to the capture portion via, for example, a protein such as biotin or streptavidin, or covalently. In some embodiments, covalent connection of the stem to the capture portion can include the capture portion being synthesized as an extension of the stem itself. This can include, for example, synthesizing both the stem and the capture region(s) as a single oligonucleotide. The capture portion can be, for example, an antibody and/or a fragment of an antibody such as, for example, Fab, F(ab')2, Fv, scFv, Fd, dAb, or the like.

The term "antibody" refers to a polypeptide of the immunoglobulin family or a polypeptide comprising fragments of an immunoglobulin that is capable of noncovalently, reversibly, and in a specific manner binding to a corresponding target (or antigen). The term includes, but is not limited to, polyclonal or monoclonal antibodies of the isotype classes IgA, IgD, IgE, IgG, and IgM, derived from human or other mammalian cells, including natural or genetically modified forms such as humanized, human, single-chain, chimeric, synthetic, recombinant, hybrid, mutated, grafted, and in vitro generated antibodies. The term encompasses conjugates, including but not limited to fusion proteins containing an immunoglobulin moiety (e.g., chimeric or bispecific antibodies or single chain Fv's (scFv's)), and fragments, such as Fab, F(ab')2, Fv, scFv, Fd, dAb and other compositions.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The variable region contains the antigen-binding region of the antibody (or its functional equivalent) and is most critical in specificity and affinity of binding. See Paul, Fundamental Immunology (2003).

Antibodies can exist as intact immunoglobulins or as any of a number of well-characterized fragments that include specific antigen-binding activity. Such fragments can be produced by digestion with various peptidases. Pepsin digests an antibody below the disulfide bonds in the hinge region to produce F(ab)' 2, a dimer of Fab which itself is a light chain joined to VH-CH1 by a disulfide bond. The F(ab)'2 can be reduced under mild conditions to break the disulfide bond in the hinge region, thereby converting the F(ab)'2 dimer into an Fab' monomer. The Fab' monomer is essentially Fab with part of the hinge region. While various antibody fragments are defined in terms of the digestion of an intact antibody, one of skill will appreciate that such fragments can be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., scFv) or those identified using phage display libraries (see, e.g., McCafferty et al. (1990) Nature 348:552-554). Methods for the preparation of antibodies are known in the art; see, e.g., Kohler & Milstein (1975) Nature 256:495-497; Kozbor et al. (1983) Immunology Today 4:72; Cole et al., Monoclonal Antibodies and Cancer Therapy, pp. 77-96. Alan R. Liss, Inc. 1985).

As used herein, the term "Fv" refers to a monovalent or bi-valent variable region fragment, and can encompass only the variable regions (e.g., VL and/or VH), as well as longer fragments, e.g., an Fab, Fab' or F(ab')2, which also includes CL and/or CH1. Unless otherwise specified, the term "Fc" refers to a heavy chain monomer or dimer comprising CH1 and CH2 regions.

The stem can include the capture structure code, which capture structure code can be embodied in a plurality of detectable molecules coupled to the stem. These detection molecules can include chemiluminescent molecules and/or fluorophores. Such fluorophores can include, for example, any dye capable of being linked to the capture structure. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FAM, FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), pyrene butyrate, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. Fluorescent dyes and fluorescent label reagents include those which are commercially available, e.g., from Invitrogen/Molecular Probes (Eugene, Oreg.) and Pierce Biotechnology, Inc. (Rockford, Ill.).

In some embodiments, each type of capture structure can be designated by a unique bar code which can comprise a unique number of fluorophores and/or a unique mixtures of types, or in other words, colors of fluorophores.

Capture structures of a shared type are all configured to bind to the same target analyte, or in other words, to bind to a desired one or several proteins or to a desired one or several pieces of nucleic acid. Thus, when targeting multiple analytes, multiple types of capture structures may be used, including, for example, a type of capture structure for each of the targeted analytes.

The fluorophores can connect to the stem via one or several branches. A branch can comprise a piece of nucleic acid and/or a polymer of a known length and configured to attach a desired number of a desired type of flowers.

A flower is a piece of nucleic acid and/or polymer that is coupled to at least one detectable molecule and/or labelled with at least one detectable molecule. In some embodiments, the detectable molecule can be at least one fluorophore, and thus a flower can be a piece of nucleic acid and/or polymer that is coupled to at least one fluorophore and/or that is labelled with at least one fluorophore. At least one fluorophore of a flower can be a specific type, or in other words, specific color of fluorophore. Thus, all of the fluorophores in a flower can be excited by excitation energy of the same wavelength and can fluoresce the same wavelength of light. In some embodiments, the piece of nucleic acid and/or polymer of a flower can be configured to bind with a specific type of nucleic acid. A branch configured to bind with this flower can include this specific type of nucleic acid such that the branch binds with desired flowers, having desired types of fluorophores.

The branches may bind to the stem via one or several anchor points, which can be, for example, oligo anchor points. This binding of the branches to the stem and/or the flowers to the branches can comprise a detection barcode.

With such capture structures including a capture structure code, the type of the capture structure can be determined by reading the capture structure code. Then, via the detection of a detector molecule, such as a detector antibody, coupled to target analyte bound to a capture structure, the presence of target analyte at the capture structure can be determined. By knowing both the type of a capture structure, and that a target analyte is bound to that capture structure, the presence of the target analyte can be determined. This can be repeated by having a plurality of different types of capture structures. Through the reading of the capture structure codes of each of the plurality of capture structures and then determining which of the capture structures has bound a target antibody, the presence and quantity of different target antibodies in a sample can be determined. Thus, the use of capture structure codes enables multiplex evaluation of multiple analytes. In some embodiments, the number of analytes simultaneously evaluable is limited by practical considerations such as, for example, a desired dynamic range, an imaging area, resolution of the system, or the like.

With reference now to FIG. 1, a schematic illustration of one embodiment of an imaging system for multiplex detection 100 is shown. In some embodiments, the system 100 can be used to perform Total Internal Reflection Fluorescence (TIRF) Microscopy, zero-mode waveguide created by placing a metal grate on top of a transparent medium, nanoparticles in a flow environment, or the like. In such an embodiment, excitation energy is provided into a sample plate 102 by the excitation source 104. The excitation energy is retained via total internal reflectance. More specifically, the excitation energy is reflected by a sample surface 103 of the sample plate 102. The reflection of the excitation energy by the sample surface 103 induces an evanescent wave or evanescent field in a limited specimen region proximate to the sample surface 103. Detector molecules such as fluorophores within this specimen region are excited by the evanescent wave and emit light via fluorescence. This emitted light can be received and/or sensed by detector 106. In some embodiments to facilitate detection of specific wavelengths of emitted light, one or several filters 108 can be used to allow only desired wavelengths to arrive at the detector. In some embodiments, a prism can split the emitted light such that desired wavelengths of emitted light are received by one or several desired detectors 106 and/or such that desired wavelengths of emitted light impinge on desired and/or predetermined portions of the detector 106.

The sample plate 102 can comprise any material that can hold the sample and capable of internal reflectance. In some embodiments, the sample plate 102 can comprise a glass plate such as, for example, a glass slide. In some embodiments, the sample plate 102 can comprise a polymer plate (e.g. acrylic plate, a polycarbonate plate, or the like.)

The excitation source 104 can comprise a source configured to generate and provide excitation energy having desired properties including, for example, desired excitation wavelength or frequency. In some embodiments, the excitation source 104 can be configured to generate a collimated beam of excitation energy. In some embodiments, the excitation source 104 can comprise, for example, one or several light bulbs, LEDs, lasers, or the like. The excitation source 104 can be configured to deliver the excitation energy to the sample plate 102 such that the excitation energy is internally reflected by the sample plate 102. This reflection of the excitation energy generates an evanescent wave having an identical frequency and/or frequency composition to the excitation energy.

The detector 106 can comprise one or several photo-detectors configured to detect light emitted by the detection molecules. In some embodiments, the one or several photo-detectors can be configured to detect fluorescence by the fluorophores. In some embodiments, the each of the one or several photo-detectors can be configured to detect a frequency of light emitted by one of the types of detector molecules and/or types of fluorophores. In some embodiments, the detector 106 can be configured to have different regions, each of which regions is configured to detect a frequency of light emitted by one of the types of detector molecules and/or types of fluorophores.

The filter 108 can comprise one or several filters. Each of the one or several filters 108 can be configured to filter light of one or several frequencies. In some embodiments, the one or several filters 108 can be configured to filter light other than that emitted by one of the types of detector molecules and/or types of fluorophores. Thus, in some embodiments, one or several of the filters 108 can be configured to allow only light corresponding to light emitted by one of the types of detectors molecules and/or types of fluorophores to pass. Thereby, the system 100 can evaluate emitted light to determine the presence of specific detection molecules and/or fluorophores on the capture structures.

In some embodiments, one or both of the excitation source 104 and the detector 106 can be communicatingly coupled to a computer 112 and/or to a processor. In some embodiments, the computer 112 and/or processor can be configured to generate signals to control operation of the excitation source 104 and/or the detector 106, and/or receive signals from the excitation source 104 and/or from the detector 106. In some embodiments, for example, the computer 112 can receive data from the detector 106 indicating detected light and/or one or several attributes of the detected light. In some embodiments, for example, the computer 112 can, based on detected light, determine locations of capture structures of the sample surface 103 of the sample plate 102, read the capture structure codes of the capture structures, and determine whether a target analyte binding to one or several capture structures.

Figure 2:
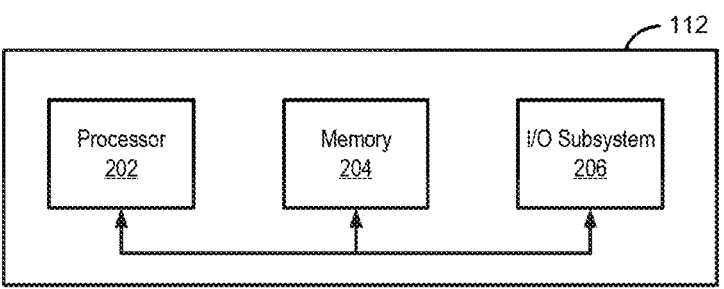
FIG. 2 is a schematic illustration of one embodiment of a computer.

With reference now to FIG. 2, a schematic illustration of one embodiment of the computer 112 is shown. The computer 112 can comprise one or several processors 202, memory 204, and an input/output ("I/O") subsystem 206.

The processor 202, which may be implemented as one or more integrated circuits (e.g., a conventional microprocessor or microcontroller), controls the operation of the computer 112 and of the other components of the system 100 including the excitation source 104 and the detector 106. One or more processors, including single core and/or multicore processors, may be included in the processor 202. Processor 202 may be implemented as one or more independent processing units with single or multicore processors and processor caches included in each processing unit. In other embodiments, processor 202 may also be implemented as a quad-core processing unit or larger multicore designs (e.g., hexa-core processors, octo-core processors, ten-core processors, or greater.

Processor 202 may execute a variety of software processes embodied in program code, and may maintain multiple concurrently executing programs or processes. At any given time, some or all of the program code to be executed can be resident in processor(s) 202 and/or in memory 204. In some embodiments, computer 112 may include one or more specialized processors, such as digital signal processors (DSPs), outboard processors, graphics processors, application-specific processors, and/or the like.

The computer 112 may comprise memory 204, comprising hardware and software components used for storing data and program instructions, such as system memory and computer-readable storage media. The system memory and/or computer-readable storage media may store program instructions that are loadable and executable on processor 202, as well as data generated during the execution of these programs.

Depending on the configuration and type of computer 112, system memory may be stored in volatile memory (such as random access memory (RAM)) and/or in non-volatile storage drives (such as read-only memory (ROM), flash memory, etc.). The RAM may contain data and/or program modules that are immediately accessible to and/or presently being operated and executed by processor 202. In some implementations, system memory may include multiple different types of memory, such as static random access memory (SRAM) or dynamic random access memory (DRAM). In some implementations, a basic input/output system (BIOS), containing the basic routines that help to transfer information between elements within computer 112, such as during start-up, may typically be stored in the non-volatile storage drives. By way of example, and not limitation, system memory may include application programs, such as client applications, Web browsers, mid-tier applications, server applications, etc., program data, and an operating system.

Memory 204 also may provide one or more tangible computer-readable storage media for storing the basic programming and data constructs that provide the functionality of some embodiments. Software (programs, code modules, instructions) that when executed by a processor provide the functionality described herein may be stored in memory 204. These software modules or instructions may be executed by processor 202. Memory 204 may also provide a repository for storing data used in accordance with the present invention.

Memory 204 may also include a computer-readable storage media reader that can further be connected to computer-readable storage media. Together and, optionally, in combination with system memory, computer-readable storage media may comprehensively represent remote, local, fixed, and/or removable storage devices plus storage media for temporarily and/or more permanently containing, storing, transmitting, and retrieving computer-readable information.

Computer-readable storage media containing program code, or portions of program code, may include any appropriate media known or used in the art, including storage media and communication media, such as, but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computer 112.

By way of example, computer-readable storage media may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media may include, but is not limited to, Zip® drives, flash memory cards, universal serial bus (USB) flash drives, secure digital (SD) cards, DVD disks, digital video tape, and the like. Computer-readable storage media may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer 112.

The input/output module 206 (I/O module 206 or I/O subsystem 206) can be configured to receive inputs from the user of the system 100 and to provide outputs to the user of the system 100. In some embodiments, the I/O subsystem 206 may include device controllers for one or more user interface input devices and/or user interface output devices. User interface input and output devices may be integral with the computer 112 (e.g., integrated audio/video systems, and/or touchscreen displays). The I/O subsystem 206 may provide one or several outputs to a user by converting one or several electrical signals to user perceptible and/or interpretable form, and may receive one or several inputs from the user by generating one or several electrical signals based on one or several user-caused interactions with the I/O subsystem 206 such as the depressing of a key or button, the moving of a mouse, the interaction with a touchscreen or trackpad, the interaction of a sound wave with a microphone, or the like.

Input devices may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices may also include three dimensional (3D) mice, joysticks or pointing sticks, gamepads and graphic tablets, and audio/visual devices such as speakers, digital cameras, digital camcorders, portable media players, webcams, image scanners, fingerprint scanners, capture structure code reader 3D scanners, 3D printers, laser rangefinders, and eye gaze tracking devices. Additional input devices may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, and the like.

Output devices may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, light-emitting diode (LED) displays, projection devices, touch screens, and the like. In general, use of the term "output device" is intended to include all possible types of devices and mechanisms for outputting information from the computer 112 to a user or other computer. For example, output devices may include, without limitation, a variety of display devices that visually convey text, graphics, and audio/video information such as monitors, printers, speakers, headphones, automotive navigation systems, plotters, voice output devices, and modems.

Figure 3:
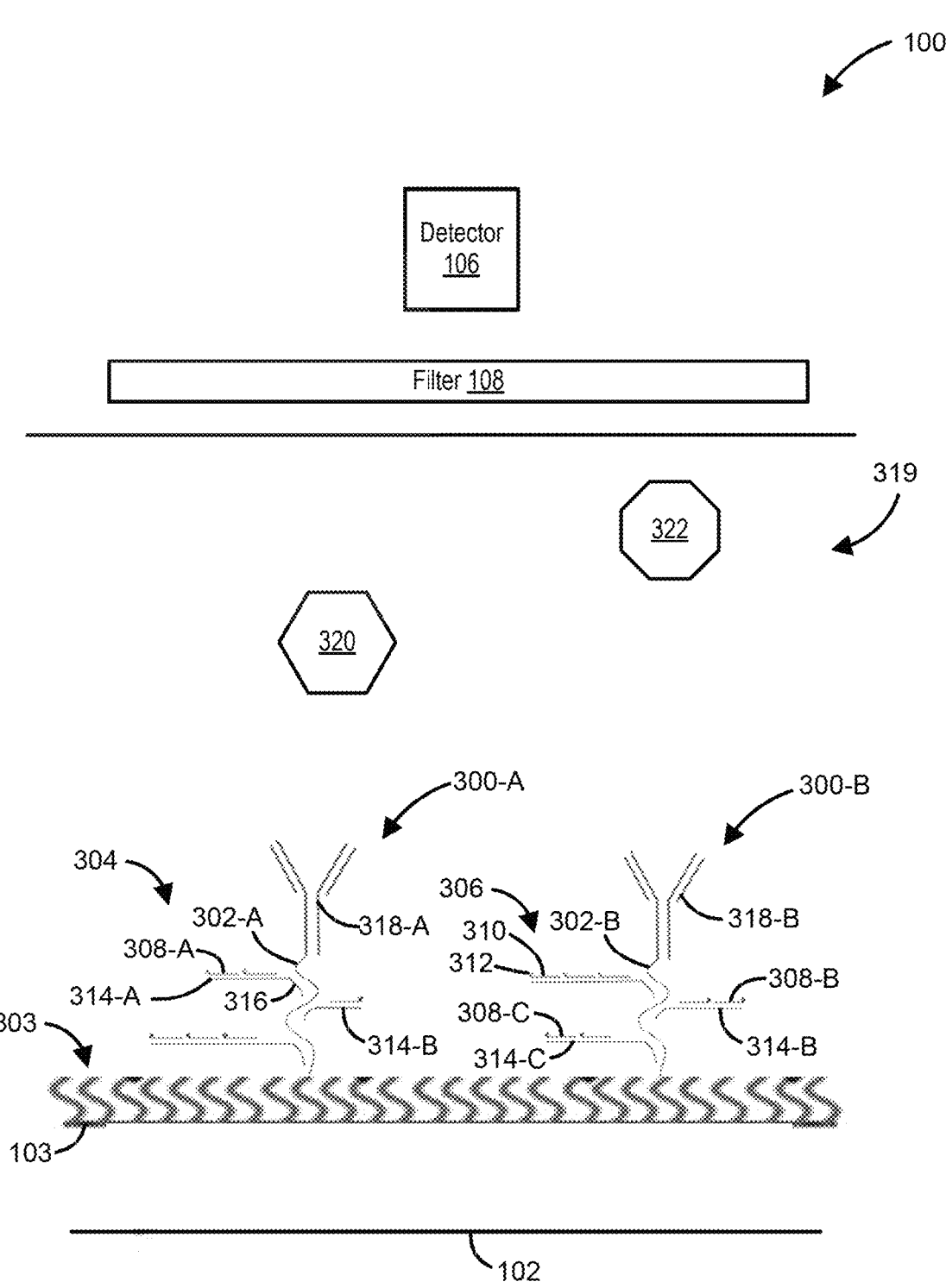
FIG. 3 is a depiction of a plurality of capture structures.
Figure 4:
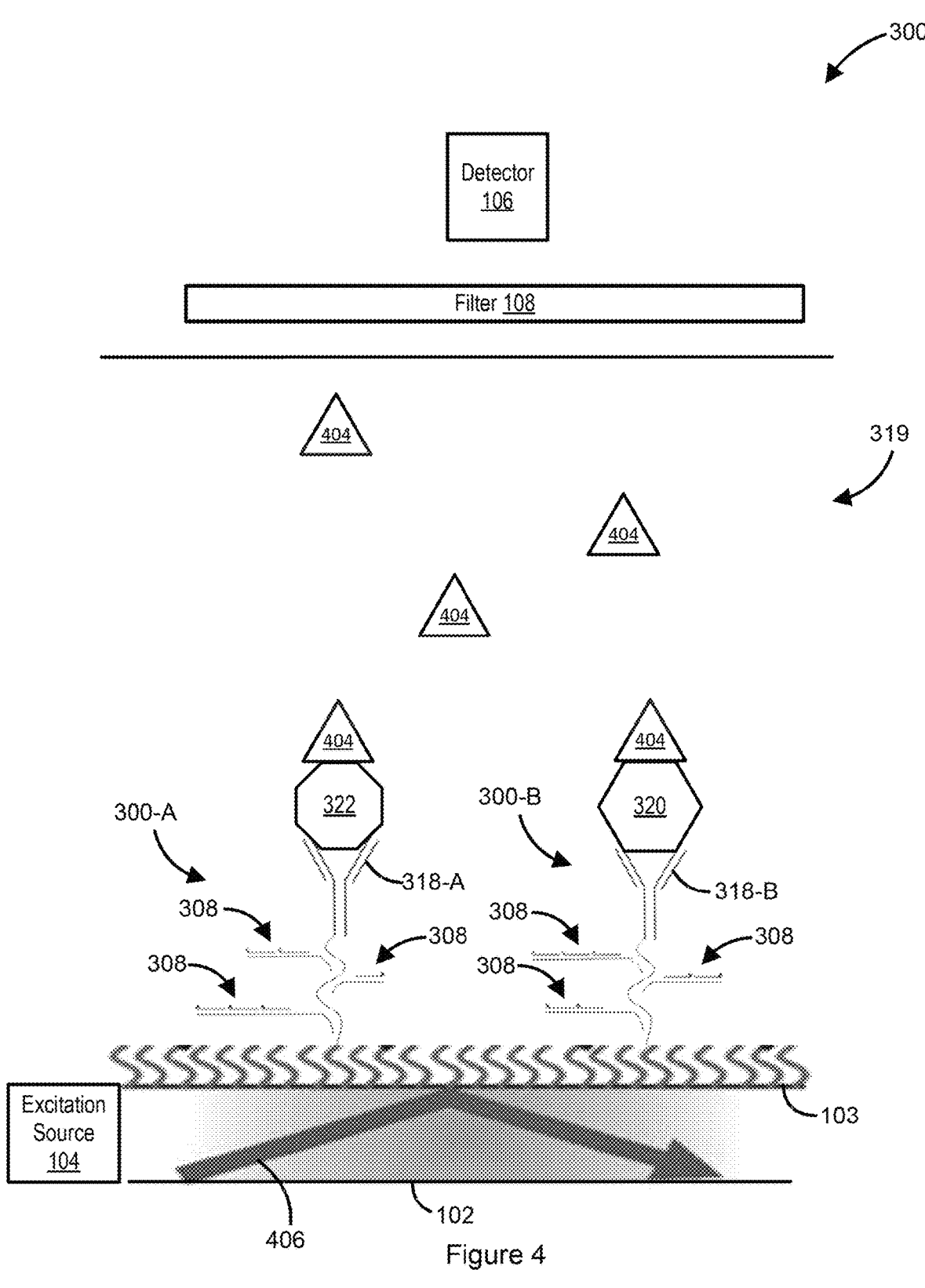
FIG. 4 is a depiction of one embodiment of imaging of a sample including a plurality of capture structures.

With reference now to FIGS. 3 and 4, a schematic depiction of aspects of multiplex detection through measurement of localized fluorescence ratios are shown. Specifically, FIG. 3 depicts a plurality of capture structures 300, and specifically depicts a first type of capture structure 300-A and a second type of capture structure 300-B. The first type of capture structure 300-A is configured to bind with a first target analyte 322, and the second type of capture structure 300-B is configured to bind with a second target analyte 320. The first target analyte 322 and second target analyte 320 can be in a sample 319.

Each of the capture structures 300 includes a stem 302. The stem 302 can comprise a strand of nucleic acid, such as, for example, a strand of DNA or a strand of RNA. In some embodiments, the stem 302 can be anything that can affix one or several branches, can bind to the sample surface 103 of the sample plate 102, and can bind to the detection portion. In some embodiments, the stem 302 can bind to the sample surface 103 of the sample plate 102 via a protein 303 such as biotin and/or streptavidin. In some embodiments, the stem 302 further keeps the detection portion, any subsequently bound target analyte and detector antibodies sufficiently close to the sample surface 103 to enable imaging via Total Internal Reflection Fluorescence (TIRF) Microscopy.

In some embodiments, the stem 302 of the first capture structure 300-A comprises a first stem 302-A and the stem 302 of the second capture structure 300-B comprises a second stem 302-B. The first stem 302-A can comprise a first capture structure code comprising a first plurality of detection molecules 304 and the second stem 302-B can comprise a second capture structure code comprising a second plurality of detection molecules 306. In some embodiments, the first stem 302-A can comprise one or several features configured to bind the first plurality of detection molecules 304 to the first stem 302-A, and the second stem 302-B can comprise one or several features configured to bind the second plurality of detection molecules 306 to the second stem 302-B.

In some embodiments, each of the capture structures 300 further comprises one or more flowers 308 coupled to the stem 302. Each of the flowers 308 can comprise a piece of nucleic acid 310 and/or polymer 310 that is coupled to, in some embodiments, at least one detectable molecule 312 and/or labelled with, in some embodiments, at least one detectable molecule. In some embodiments, the flower 308 can comprise a number of detectable molecules including, for example, 0, 1, 2, 3, 4, 5, 6, 7, 8, 9, 10, 20, 50, 100, or any other or intermediate number of detectable molecules. In some embodiments, the detectable molecule 312 can be at least one fluorophore, and thus a flower can be a piece of nucleic acid 310 and/or polymer 310 that is coupled to at least one fluorophore and/or that is labelled with at least one fluorophore.

The detection molecules 312 can comprise, for example fluorophores. In some embodiments, the detection molecules 312 can comprise a number of types of detection molecules 312, or more specifically, a number of types of fluorophores. In some embodiments, each type of capture structure 300 can include and/or be configured to include a unique set of detection molecules 312 which can together form a capture structure code uniquely identifying that type of capture structure 300.

If present, the fluorophores of a flower 308 can all be a specific type, or in other words, specific color of fluorophore. Thus, all of the fluorophores in a flower 308 can be excited by excitation energy of the same wavelength and can fluoresce the same wavelength of light. In some embodiments, the piece of nucleic acid 310 and/or polymer 310 of a flower 308 can be configured to bind with a specific type of nucleic acid that can be found in at least a portion of the capture structure 300. In some embodiments, a portion of the capture structure 300 can include this specific type of nucleic acid such that the portion of the capture structure 300 binds with desired types and numbers of flowers 308, having desired types of detection molecules 312. In some embodiments, the fluorophore(s) can be linked directly to the branches rather than through the flower.

In some embodiments, and as shown in FIG. 3, this can include a first type of flower 308-A, a second type of flower 308-B, and a third type of flower 308-C. In some embodiments, each of these different types of flowers 308 can emit a detectable signal that is distinguishable from the detectable signals of other types of flowers 308. This can include, for example, the different types of flowers 308 including different types of fluorophores emitting different wavelengths of light, whereby the different types of fluorophores can be distinguished from each other.

The presence or absence of these different types of detection molecules 312 coupled to a stem 302, and/or the number of these detection molecules 312 coupled to a stem 302 can create the capture structure code. As seen in FIG. 3, for example, the first capture structure 300-A includes different numbers of different types of flowers 308 than the second capture structure 300-B. Specifically, the first capture structure 300-A includes two of a first type of flower 308-A, one of a second type of flower 308-B, and three of a third type of flower 308-C. In contrast to this, the second capture structure 300-B includes three of the first type of flower 308-A, two of the second type of flower 308-B, and two of the third type of flower 308-C. Thus, by detecting the different numbers and/or types flower 308 of a capture structure 300, or in other words, reading the capture structure code of the capture structure 300, the type of the capture structure 300 can be identified.

The flowers 308 can, in some embodiments, be coupled to one or several branches 314. In some embodiments, each of the branches 314 can comprise a piece of nucleic acid and/or a polymer of a known length and configured to attach a desired number of a desired type of flowers 308. In some embodiments, for example, a branch 314 can be configured to couple with any desired number of flowers 308 including, for example, 0 flowers, 1 flower, 2 flowers, 3 flowers, 4 flowers, 5 flowers, 6 flowers, 7 flowers, 10 flowers, 20 flowers, 50 flowers, or any other or intermediate number of flowers. The branches 314 can couple to the stem 302 at an anchor point, which can be an oligo anchor point. This binding of the branches 314 to the stem 302 and/or the flowers 308 to the branches 314 can comprise nucleotide binding.

In some embodiments, the branches 314 can include a branch 314 specific for each type of flower 308. Thus, as depicted in FIG. 3, the branches 314 can include a first branch 314-A for binding with first flowers 308-A, a second branch 314-B for binding with second flowers 308-B, and a third branch 314-C for binding with third flowers 308-C. The anchor points 316 of the stems 302 can be specific to one of the branch types. Thus, for example, a first anchor point 316 can be configured for binding with a first branch 314-A, a second anchor point 316 can be configured for binding with a second branch 314-B, and a third anchor point 316 can be configured for binding with a third branch 314-C. In some embodiments, the anchor points 316 can be further specific for binding with a branch of a specific branch type and of a specific length. Thus, for example, the anchor point 316 of the first capture structure 300-A can be configured to bind to the first branch 314-A having a length for receiving two flowers 308. Thus, through the inclusion of branch-specific anchor points 316, a stem 302 can bind with desired branches 314, which branches can then bind with desired type of flowers 308 and/or the desired number of the desired type of flowers 308, thereby creating the desired capture structure code for that capture structure 300.

The capture structures 300 can further include a detection portion 318. Specifically, the first type of capture structure 300-A includes a first type of detection portion 318-A, and the second type of capture structure 300-B includes a second type of detection portion 318-B. In some embodiments, the first detection portion 318-A can be configured for binding with the first target analyte 322, and the second detection portion 318-B can be configured for binding with the second target analyte 320. In some embodiments, the detection portions 318 can connect to stem 302 via, for example, a protein such as biotin or streptavidin, or covalently. The detection portion 318 can be, for example, an antibody.

FIG. 4 depicts imaging of the sample 319. As seen, the first target analyte 322 is captured by the first capture structure 300-A, and specifically by the first detection portion 318-A, and the second target analyte 320 is captured by the second capture structure 300-B, and specifically by the second detection portion 318-B.

As further seen in FIG. 4, detector molecules 404, which detector molecules 404 can be detector antibodies, have been added to the sample 319. These detector molecules 404 can transiently or permanently bind with the target analytes 320, 322 bound to their corresponding capture structure 300.

The excitation source 104 can be controlled to generate excitation energy, which excitation energy can be directed into the sample plate 102. The excitation energy can comprise electromagnetic radiation, and specifically can comprise light 406 which can be internally reflected by the sample plate 102. The reflection of the light 406 off the sample surface 103 can generate an evanescent wave that can excite the flowers 308 and/or the detector molecules 404 coupled to the target analytes 320, 322.

The detector 106 can detect light from the detector molecules 404 coupled to the target analytes 320, 322 and from the flowers 308. The detector 106 can provide information to the computer 112 and/or processor which can, determine the location of the capture structures 300, read the capture structure code of each of the capture structures 300 via detecting the fluorescence of the flowers 308, and identify capture structures 300 that have captured a target analyte 320, 322. Based on this information, the computer can determine the presence and quantity of target analyte 320, 322 in the sample 319.

Figure 5:
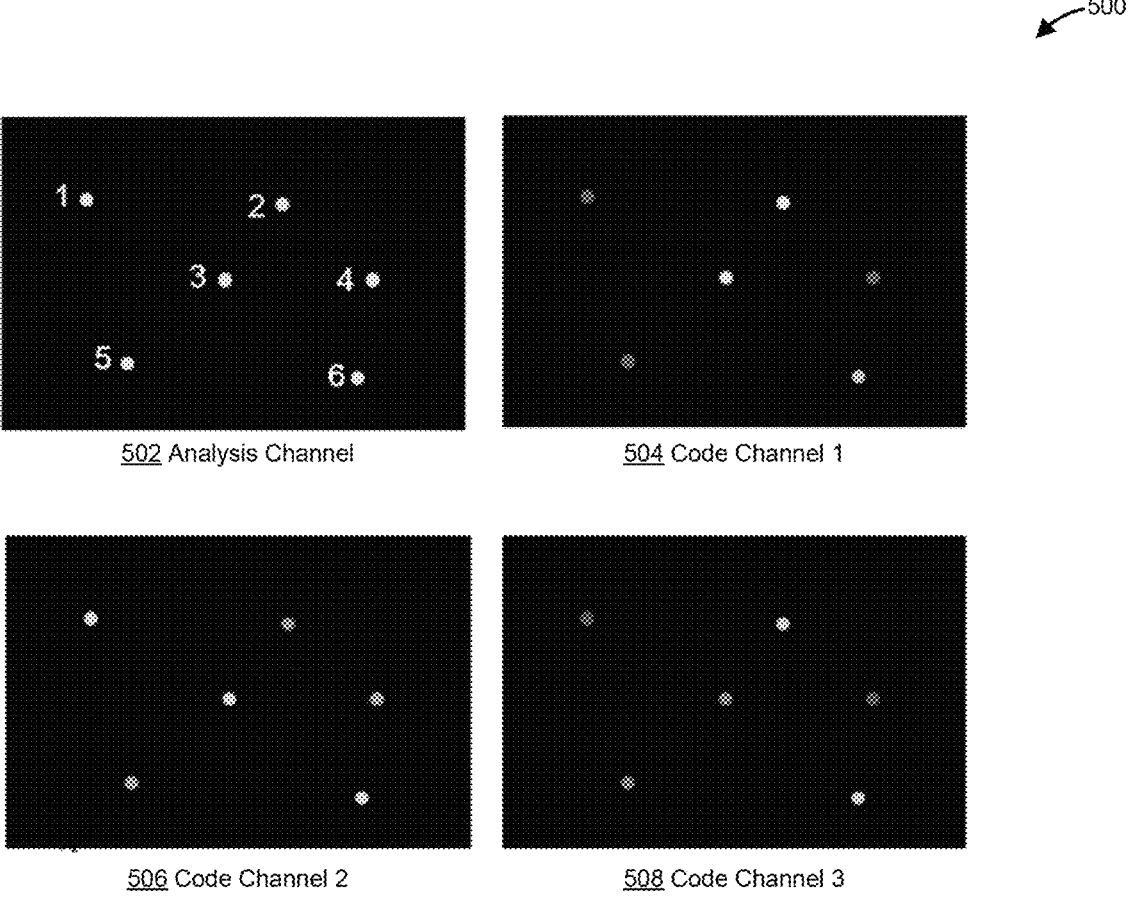
FIG. 5 is a depiction of one embodiment of hypothetical imaging results.

With reference now to FIG. 5, a depiction of hypothetical imaging results is shown. Specifically, FIG. 5 shows an example of light imaged by the detector 106 across four channels. These four channels can be collected in any order. The collection of these four channels can: identify the location of capture structures 300 affixed to the sample surface 103, determine the presence of target analyte at those locations; and read the capture structure code of the capture structures 300 affixed to the sample surface 103.

The four channels include a first channel, which first channel is an analysis channel 502. The analysis channel 502 can image light from detector molecules 404 bound with target analytes 320, 322 likewise bound to a capture structures 300. In some embodiments, the analysis channel 502 can be generated via imaging such as, for example, SIM-REPS imaging such as, for example SIMREPS generated using Foerster Resonance Energy Transfer (FRET), or the like. As seen in FIG. 5, there are six locations detected as having detector molecules 404 bound with target analytes 320, 322 likewise bound to a capture structures 300.

The four channels include a second channel, which second channel is code channel 1 504. Code channel 1 504 can comprise a channel configured to read a portion of the capture structure code of the capture structures 300 bound to the sample surface 103. This can include detecting light emitted by the flowers 308 of the capture structures 300, and specifically determining presence and/or quantity of types of flowers for the capture structures 300 bound to the sample surface by detecting, quantifying, and evaluating certain wavelengths/frequencies of light detected by the detector 106. In some embodiments, code channel 1 504 can image, capture, and/or detect light of a first frequency and/or first range of frequencies. In some embodiments, this light of the first frequency and/or of the first range of frequencies can correspond to a color, such as, for example, red.

As seen in FIG. 5, the intensity of the light captured by the detector 106 in code channel 1 varies between the six locations, with points 1, 4, and 5 generating the most intense signal (e.g. the most red signal), points 2 and 3 generating the least intense signal (e.g. the least red signal), and point 6 generating an intermediate signal.

The four channels include a third channel, which third channel is code channel 2 506. Code channel 2 506 can comprise a channel configured to read a portion of the capture structure code of the capture structures 300 bound to the sample surface 103. This can include detecting light emitted by the flowers 308 of the capture structures 300, and specifically determining presence and/or quantity of flowers 308 of the capture structures 300 bound to the sample surface by detecting, quantifying, and evaluating certain wavelengths/frequencies of light detected by the detector 106. In some embodiments, code channel 2 506 can image, capture, and/or detect light of a second frequency and/or of a second range of frequencies. In some embodiments, this light of the second frequency and/or of the second range of frequencies can correspond to a color, such as, for example, green.

As seen in FIG. 5, the intensity of the light captured by the detector 106 in code channel 2 506 varies between the six locations, with points 4 and 5 generating the most intense signal (e.g. the most green signal), points 1, 3, and 6 generating the least intense signal (e.g. the least green), and point 2 generating an intermediate signal.

The four channels include a fourth channel, which fourth channel is code channel 3 508. Code channel 3 508 can comprise a channel configured to read a portion of the capture structure code of the capture structures 300 bound to the sample surface 103. This can include detecting light emitted by the flowers 308 of the capture structures 300, and specifically determining presence and/or quantity of flowers 308 of the capture structures 300 bound to the sample surface by detecting, quantifying, and evaluating certain wavelengths/frequencies of light detected by the detector 106. In some embodiments, code channel 2 506 can image, capture, and/or detect light of a third frequency and/or of a third range of frequencies. In some embodiments, this light of the third frequency and/or of the third range of frequencies can correspond to a color, such as, for example, blue.

As seen in FIG. 5, the intensity of the light captured by the detector 106 in code channel 3 508 varies between the six locations, with points 1 and 4 generating the most intense signal (e.g. the most blue signal), points 2 and 6 generating the least intense signal (e.g. the least blue), and points 3 and 5 generating an intermediate signal.

In some embodiments, each of code channel 1 504, code channel 2 506, and code channel 3 508 can image different frequencies and/or different ranges of frequencies. In some embodiments, for example, these different frequencies and/or different ranges of frequencies can be distinct in that they do not include any overlap or can be partially distinct in that they only partially overlap. Although FIG. 5 depicts 3 code channels 504, 506, 508, other embodiments can include fewer code channels or more code channels. In some embodiments, the number of channels can be limited by the number of different types of detection molecules that can be differentiated by detector 106.

The data collected by the detector can be evaluated to determine locations of capture structures 300 bound to the sample surface 103 and to read the capture structure code of those capture structures 300. This can include determining the presence or absence of different types of flowers 308 at locations of the different capture structures 300, and if a type of flower 308 is present at a location of a capture structure 300 affixed to the sample surface 103, quantifying that type of flower at the location of the capture structure 300 affixed to the sample surface 103.

The data output by the detector 106 can be stored in the computer 112, and specifically can be stored in memory 204. This data can be stored in one or several databases in the memory 204. This data can be evaluated by the computer 112, and specifically by the processor 202. In some embodiments, the data, and specifically the data gathered via the code channels 504, 506, 508 can be evaluated by the computer 112 to extract the capture structure code for each of the capture structures 300. Based on this evaluation, the computer 112 can determine types of flowers 308 associated with each of the capture structures 300, and the number of each of the types of flowers 308 associated with each of the capture structures 300.

Figure 6:
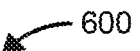
FIG. 6 is a table showing numbers of flowers and/or flower clusters based on data gathered from a plurality of code channels.

Such a determination of the number of each type of flowers 308 associated with capture structures 300 is depicted in FIG. 6. Specifically, FIG. 6 is a table 600 showing numbers of flowers 308 and/or flower clusters based on data gathered from the code channels 504, 506, 508 in FIG. 4. As seen, location 1 has 3 flowers 308 or flower clusters of the flower type associated with channel 1, 1 flower 308 or flower cluster of the flower type associated with channel 2, and 3 flowers 308 or flower clusters of the flower type associated with channel 3. Similarly, location 3 has 1 flower 308 or flower cluster of the flower type associated with channel 1, 1 flower 308 or flower cluster of the flower type associated with channel 2, and 2 flowers 308 or flower clusters of the flower type associated with channel 3, and location 6 has 2 flowers 308 or flower clusters of the flower type associated with channel 1, 1 flower 308 or flower cluster of the flower type associated with channel 2, and 1 flower 308 or flower cluster of the flower type associated with channel 3. The number of flowers 308 or flower clusters of each type and for each location are further depicted in FIG. 6 The data for a location represented in FIG. 6 can be the capture structure code of that location and/or the capture structure code of the capture structure 300 at that location.

In some embodiments, and to increase the robustness of the capture structure code, flower clusters can be identified. A flower cluster can comprise a plurality of flowers 308 of the same type. Thus, a branch 314 might include or be coupled to one or several flower clusters, each of which can comprise a plurality of flowers. By counting flower clusters, instead of individual flowers 308, the multiplex detection becomes more robust in the event that a number of flowers do not properly couple with the branch 314.

With reference now to FIG. 7, a flowchart illustrating one embodiment of a process 700 for multiplex detection is shown. The process can be performed by all portions of the system 100. The process 700 begins at block 702, wherein capture structures 300 are created. In some embodiments, this can include mixing stems 302 corresponding to desired types of capture structures 300 with branches 314, flowers 308, and detection portions 318 corresponding to the desired types of capture structures 300. In some embodiments, branches 314 can connect to appropriate anchor points 316 on stems 302, and flowers 308 can couple to appropriate branches 314. Similarly, detection portions 318 can couple to the appropriate stem 302. In some embodiments, this can include mixing the stems 302, flowers, 308, branches 314, and/or detection portions 318 together in mixing liquid in one or several containers, vials and/or on the sample plate 102, and providing an amount of time for the forming of the capture structures 300

After the capture structures 300 have been created, the process 700 proceeds to block 704, wherein a sample containing one or several target analytes, also referred to herein as analytes of interest, is mixed with the capture structures 300. In some embodiments, the capture structures 300 can be mixed with the solution containing one or several target analytes in one or several containers, vials, and/or on the sample plate 102. In some embodiments, this can include providing time for the analyte of interest to be captured by the one or several capture structures 300.

At block 706, the capture structures 300 are attached to the sampling surface 103. In some embodiments, this can occur by applying the mixture containing the capture structures 300 to the sampling surface 103, and providing time for the capture structures 300 to bind to the sampling surface 103. In some embodiments, the step of block 706 can be performed before the step of block 704.

At block 708 the sampling surface 103 can optionally be washed. At block 710, the location of capture structures 300 on the sample surface 103 can be identified, and the capture structure codes of the capture structures 300 can be read. In some embodiments, reading of the capture structure codes can include the identification of the locations of the capture structures 300 on the sample surface. In some embodiments, reading the capture structure codes of the capture structures 300 can include generating excitation energy with the excitation source 104 and capturing light emitted by the flowers 308 of the capture structures 300 with the detector 106. The capturing of light emitted by the flowers 308 of the capture structures 300 can include capturing image data across multiple channels, and specifically across multiple code channels such as code channels 504, 506, 508. The computer 112 can then evaluate the captured image data and/or the detected light emitted by the flowers 308 to determine the number of flowers 308 and/or flower clusters at each location of a capture structure 300 on the sample surface. This can result in a determination of which types of flowers 308 and/or flower clusters are coupled to each capture structure 300, and the number of flowers 308 and/or flower clusters coupled to those capture structures 300.

At block 712 detector molecules 404, which can be detector antibodies, are added. In some embodiments, these detector molecules 404 can be mixed with the capture structures 300 and the target analyte such that the detector molecules 404 can bind with target analyte coupled to a capture structure as shown in FIG. 4. In some embodiments, this step can be performed before the capture structures 300 are attached to the sampling surface 103 as shown in block 706, and in some embodiments, and as shown in FIG. 7, the step of block 712 can be performed after the capture structures 300 are attached to the sampling surface 103 as shown in block 706. In some embodiments, this step can be performed before the locations of the capture structure are identified and/or before the encoding of the capture structures is read as shown in block 710.

At block 714, locations containing a properly bound target analyte and/or capture structures containing a properly bound target analyte are determined. In some embodiments, this determination can include delivery of excitation energy via the excitation energy source 104 and the sensing of emitted light with the detector 106 which can generate data based on the sensed emitted light. In some embodiments, this data can be captured and/or generated via one of the channels, and specifically via, for example, the analysis channel 502. In some embodiments, the data of the analysis channel 502 can be generated via imaging such as, for example, SIMREPS imaging, and/or SIMREPS imaging with FRET. In some embodiments, the steps of blocks 712 and 714 can be performed before the locations of the capture structure are identified and/or before the encoding of the capture structures is read as shown in block 710.

At block 716 a number of target analytes in the sample and/or the concentration of target analytes in the sample is determined. In some embodiments, this can be based on the determined capture structures 300 containing a properly bound target analyte, and the capture structure codes of those capture structure 300. More specifically, in some embodiments, this can include determining the number of capture structures 300 containing target analytes, determining the capture structure code of those capture structures 300, grouping capture structures 300 having a common capture structure code, and counting the number of capture structures 300 in each group. In some embodiments, the computer 112 can determine the number of target analytes in the sample.

At block 718, the number and/or concentration of target analytes in the sample is output. In some embodiments, this can include outputting the number and/or concentration of target analytes via the computer 112, and specifically via the I/O subsystem 206.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A system for detecting one or more target analytes in a sample the system comprising:
   a sample plate configured to hold the sample on a sample plate surface, the sample plate comprising a plurality of capture structures attached to the sample plate surface, each of the plurality of capture structures independently comprising:
      a detection portion configured to couple with a target analyte of the one or more target analytes; and
      a stem comprising a capture structure code, the capture structure code comprising a plurality of flowers, each independently comprising a piece of nucleic acid or polymer coupled to at least one detectable molecule, wherein the detectable molecules embody the capture structure code, and wherein the detectable molecules in combination uniquely identify a type of the capture structure associated with the detection portion;
   an excitation source configured to generate excitation energy delivered into the sample plate;
   a detector configured to detect light emitted by the detectable molecules; and
   a hardware processor operably connected to the detector and configured, when executing instructions stored in a memory, to:
      determine a location of each of the capture structures on the sample plate surface;
      read the capture structure code of each of the capture structures;
      determine a location at which a target analyte is bound to one of the capture structures; and
      determine the target analyte based on the capture structure code of the capture structure at the location at which the target analyte is bound to one of the capture structures.

2. The system of claim 1, wherein each of the target analytes comprises at least one of: a protein; or a strand of nucleic acid.

3. The system of claim 1, wherein the detection portion of one or more of the capture structures comprises an antibody.

4. The system of claim 1, wherein each of the plurality of flowers comprises a piece of nucleic acid coupled to at least one detectable molecule, the at least one detectable molecule comprising a fluorophore.

5. The system of claim 1, wherein each of the plurality of flowers comprises a piece of polymer coupled to at least one detectable molecule.

6. The system of claim 1, wherein each of the plurality of flowers comprises one of: a single flower; or a cluster of flowers.

7. The system of claim 1, wherein each of the plurality of flowers is coupled to the stem via at least one branch.

8. The system of claim 7, wherein the at least one branch comprises a strand of nucleic acid, the strand of nucleic acid comprising a known length and configured for attaching a desired number of flowers.

9. The system of claim 7, wherein the at least one branch comprises a strand of nucleic acid, wherein the strand of nucleic acid comprises at least one of: a strand of DNA; or a strand of RNA.

10. The system of claim 7, wherein the at least one branch comprises a polymer of known length and configured for attaching a desired number of flowers.

11. The system of claim 1, wherein the plurality of flowers comprise at least two colors of flowers, wherein the flowers of each of the at least two colors are coupled to the stem via a unique at least one branch.

12. The system of claim 11, wherein reading the capture structure code of each of the capture structures comprises:

for the location of each of the capture structures on the sample plate surface, gathering light from the flowers coupled to the stem of the capture structure at that location; and determining a number and color of flowers attached to the stem of the capture structure.

13. The system of claim 12, wherein the light from the flowers coupled to the stem of the capture structure at that location is gathered by a detector, and wherein determining the number and color of flowers attached to the stem of the capture structure comprises evaluating a plurality of channels of data from the detector.

14. The system of claim 13, wherein evaluating the plurality of channels of data from the detector comprises evaluating light intensity at locations of capture structures attached to the sample plate surface in each of the plurality of channels, wherein the processor is further configured to determine a number of target analytes in the sample.

15. The system of claim 14, wherein determining the number of target analytes in the sample comprises:

determining the number of capture structures bound to target analytes;

determining the capture structure code of each of the capture structures bound to target analytes;

grouping capture structures having a common determined capture structure code; and counting the number of capture structures in each group.

16. The system of claim 15, wherein the processor is further configured to output the number of target analytes in the sample.

17. The system of claim 1, wherein each type of capture structure is associated with a unique combination of number of types of flowers.

18. The system of claim 17, wherein a first type of capture structure comprises a first number of a first type of flowers and a second number of a second type of flowers, wherein a second type of capture structure comprises a third number of the first type of flowers and a fourth number of a third type of flowers, and wherein the second type of capture structure comprises none of the second type of flowers.

19. A method for detecting one or more target analytes in a sample, the method comprising:

creating a plurality of capture structures, each of the plurality of capture structures independently comprising a detection portion and a stem, the detection portion configured to couple with a target analyte of the one or more target analytes, and the stem comprising a capture structure code, the capture structure code comprising a plurality of flowers, each independently comprising a piece of nucleic acid or polymer coupled to at least one detectable molecule, wherein the detectable molecules embody the capture structure code, and wherein the detectable molecules in combination uniquely identify a type of the capture structure associated with the detection portion;

attaching each of the capture structures to a sample plate surface;

mixing the plurality of capture structures with the sample;

determining a location of each of the capture structures on the sample plate surface;

reading the capture structure code of each of the capture structures;

determining a location at which a target analyte is bound to one of the capture structures; and determining the target analyte based on the capture structure code of the capture structure at the location at which the target analyte is bound to one of the capture structures.

* * * * *